United States Patent
Fondeur et al.

(10) Patent No.: US 10,598,599 B2
(45) Date of Patent: Mar. 24, 2020

(54) METHODS AND MATERIALS FOR DETERMINATION OF DISTRIBUTION COEFFICIENTS FOR SEPARATION MATERIALS

(71) Applicant: Savannah River Nuclear Solutions, LLC, Aiken, SC (US)

(72) Inventors: Fernando F. Fondeur, N. Augusta, SC (US); Simona H. Murph, N. Augusta, SC (US); Kathryn L. Taylor-Pashow, Aiken, SC (US); David T. Hobbs, N. Augusta, SC (US)

(73) Assignee: Savannah River Nuclear Solutions, LLC, Aiken, SC (US)

( * ) Notice: Subject to any disclaimer, the term of this patent is extended or adjusted under 35 U.S.C. 154(b) by 310 days.

(21) Appl. No.: 14/930,966

(22) Filed: Nov. 3, 2015

(65) Prior Publication Data

US 2017/0122875 A1 May 4, 2017

(51) Int. Cl.
*G01N 21/65* (2006.01)
*B01D 15/36* (2006.01)
(Continued)

(52) U.S. Cl.
CPC ......... *G01N 21/658* (2013.01); *B01D 15/363* (2013.01); *B01J 20/0233* (2013.01);
(Continued)

(58) Field of Classification Search
None
See application file for complete search history.

(56) References Cited

U.S. PATENT DOCUMENTS

| 4,156,646 A | 5/1979 | Schulz |
| 6,268,307 B1 | 7/2001 | DeFilippi et al. |

(Continued)

FOREIGN PATENT DOCUMENTS

| EP | 1040869 A2 | 10/2000 |
| EP | 1048660 | 11/2000 |

(Continued)

OTHER PUBLICATIONS

Barr, M. E. New Anion-Exchange Resins for Improved Separations of Nuclear Materials, 1997, Mid-Year Progress Report. Los Alamos National Laboratory, retrieved from internet : http://www.iaea.org/inis/collection/NCLCollectionStore/_Public/31/003/31003268.pdf.*

(Continued)

*Primary Examiner* — Xiaoyun R Xu
(74) *Attorney, Agent, or Firm* — Dority & Manning, P.A.

(57) ABSTRACT

Methods and materials for determining the affinity of separation materials for targeted species are described. A composite separation medium is described that combines a separation material such as an ion exchange material or a sorbent with an SERS substrate. Methods and materials can be utilized to determine the distribution coefficient of a species for a separation material after running a single separation protocol followed by examination of the separation material of the protocol according to SERS. Disclosed methods can be utilized to determine the affinity of existing separation materials for targeted species as well as to determine the affinity of newly engineered separation materials to characterize species.

16 Claims, 5 Drawing Sheets

(51) Int. Cl.
  *G21F 9/12* (2006.01)
  *B01J 20/12* (2006.01)
  *B01J 20/28* (2006.01)
  *B01J 20/02* (2006.01)
  *B01J 47/016* (2017.01)

(52) U.S. Cl.
  CPC ......... *B01J 20/12* (2013.01); *B01J 20/28007* (2013.01); *B01J 47/016* (2017.01); *G21F 9/12* (2013.01); *B01J 2220/42* (2013.01)

(56) References Cited

U.S. PATENT DOCUMENTS

| | | | |
|---|---|---|---|
| 7,494,640 | B1 | 2/2009 | Nyman et al. |
| 2003/0035772 | A1 | 2/2003 | Sylvester |
| 2003/0212283 | A1 | 11/2003 | Parker et al. |
| 2006/0226081 | A1 | 10/2006 | Lupton et al. |
| 2008/0145450 | A1 | 6/2008 | Hobbs et al. |
| 2009/0168059 | A1* | 7/2009 | Farquharson ............ G01N 1/40 356/301 |
| 2014/0072804 | A1 | 3/2014 | Hobbs et al. |

FOREIGN PATENT DOCUMENTS

| | | |
|---|---|---|
| WO | WO97/14652 | 4/1997 |
| WO | WO2013/176956 | 11/2013 |

OTHER PUBLICATIONS

Tessier, P.M. et al. On-Line Spectroscopic Characterization of Sodium Cyanide with Nanostructured Gold Surface-Enhanced Raman Spectroscopy Substrates, 2002, Applied Spectroscopy, vol. 56(12), pp. 1524-1530.*

Fondeur, F.F. et al. Sorption Modeling of Strontium, Plutonium, Uranium and Neptunium Adsorption on Monosodium Titanate, 2003, retrieved from internet site: file:///C:/Users/xxu/Documents/e-Red%20Folder/14930966/Fondeur%202003.pdf.*

WikipediA retrieved from internet site: https://web.archive.org/web/20130210121214/https://en.wikipedia.org/wiki/Normal_distribution (Year: 2013).*

Nyman, et al.; "A Family of Peroxo-titanate Materials Tailored for Optimal Strontium and Actinide Sorption," WSRC-STI-2006-00077; (2006) (30 pages).

Mullen, et al.; "Trace Detection of Ionic Species with Surface Enhanced Raman Spectroscopy," Journal Article WWRC-92-03; *Spectroscopy*, vol. 7, 1992, 10 pages.

Fisk, et al. "Achieving optimal SERS through enhanced experimental design" *J. Raman Spetrosc.* 47(2016) pp. 59-66.

Long, et al. "Reproducible Ultrahigh SERS Enhancement in Single Deterministic Hotspots Using Nanosphere-Plane Antennas Under Radially Polarized Excitation" *Scientific Reports* 6:33218 (2016) pp. 1-8.

Pelletier, M.J. "Quantitative Analysis Using Raman Spectrometry" *Applied Spectroscopy* 57(1)(2003) pp. 20A-42A.

Postaci, et al. "Silent enhancement of SERS signal without increasing hot spot intensities" *Nanophotonics* 7(10) (2018) pp. 1687-1695.

Shaw, et al. "Statistical Correlation Between Sers Intensity and Nanoparticle Cluster Size" *J. Phys. Chem.* 117 (2013) pp. 16596-16605.

Slot, et al. "Sizing of Protein A-Colloidal Gold Proteins for Immunoelectron Microscopy" *J. Cell Biol.* 90 (1981) pp. 533-536.

Demirörs, et al. "A General Method to Coat Colloidal Particles with Titania" *Langmuir* 26(12) (2010) pp. 9297-9303.

Du, et al. "Photosynthetic Bacterial Light-Harvesting Antenna Complexes Adsorbed on Silica Nanoparticles Revealed by Silica Shell-Isolated Au Nanoparticle SERS" *J. Phys. Chem. C* 116 (2012) pp. 6993-6999.

Gellner, et al. "Optical Properties and SERS Efficiency of Tunable Gold/Silver Nanoshells" *Vibrat. Spectro.* 50 (2009) pp. 43-47.

Haynes, et al. "Surface-Enhanced Raman Spectroscopy" *Analyt Chem.* (2005) pp. 339A-344A.

Ignat, et al. "Nanostructured Au/Si Substrate for Organic Molecule SERS Detection" *Superlatt. Microstruct.* 46 (2009) pp. 451-460.

Lee, et al. "Protein-Based SERS Technology Monitoring the Chemical Reactivity on a Synuclein-Mediated Two-Dimensional Array of Gold Nanoparticles" *Langmuir* 27 (2011) pp. 12782-12787.

Link, et al. "Size and Temperature Dependence of the Plasmon Absorption of Colloidal Gold Nanoparticles" *J. Phys. Chem.* 8(103) (1999) pp. 4212-4217.

Nash, et al. "Phase I Technical Report for the Engineering of Monosodium Titanate" WSRC-TR-2004-00286 *Savann. Riv. Site* (2004) pp. 1-64.

Sarsfield, et al. "Raman Spectroscopy of Plutonium Dioxide and Related Materials" *J. Nucl. Mater.* 427 (2012) pp. 333-342.

Shen, et al. "Nanospheres of Silver nanoparticles: Agglomeration, Surface Morphology Control and Application as SERS Substrates" *Phys. Chem. Chem. Phys.* 11 (2009) pp. 7450-7454.

Su, et al. "Interparticle Coupling Effects on Plasmon Resonances of Nanogold Particles" *Nanoletters* 3(8) (2003) pp. 1087-1090.

Yu, et al. "Synthesis of Au/TiO$_2$ Core-Shell Structure Nanoparticles and the Crystallinity of TiO$_2$ Shell" *Mater. Trans.* 45(3) (2004) pp. 964-967.

* cited by examiner

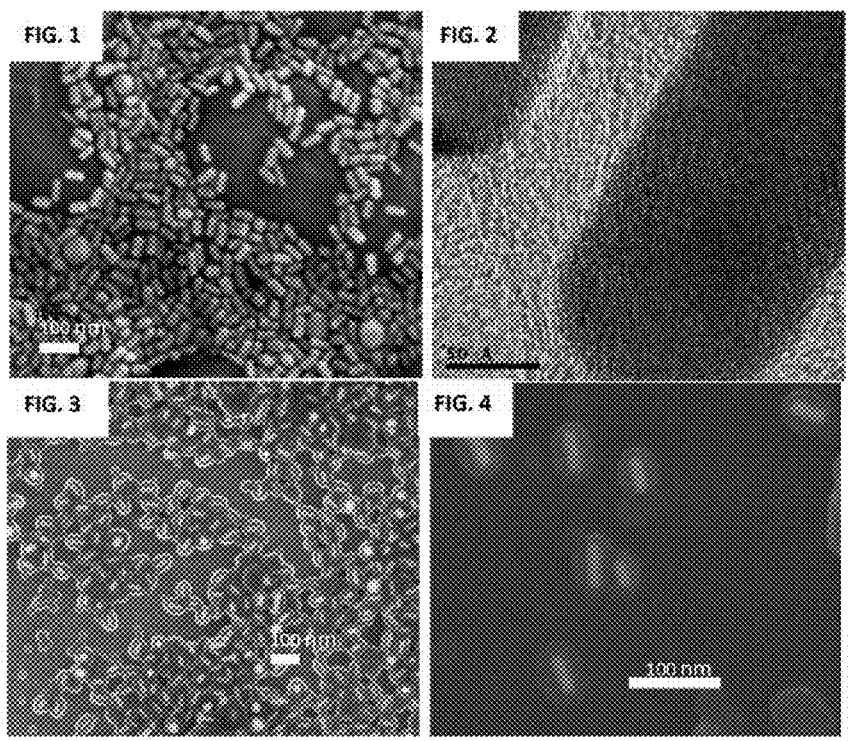
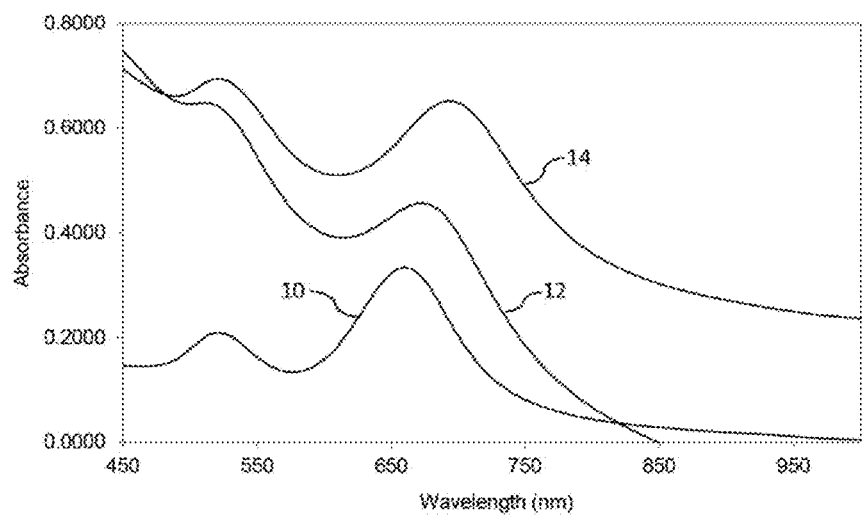
FIG. 5

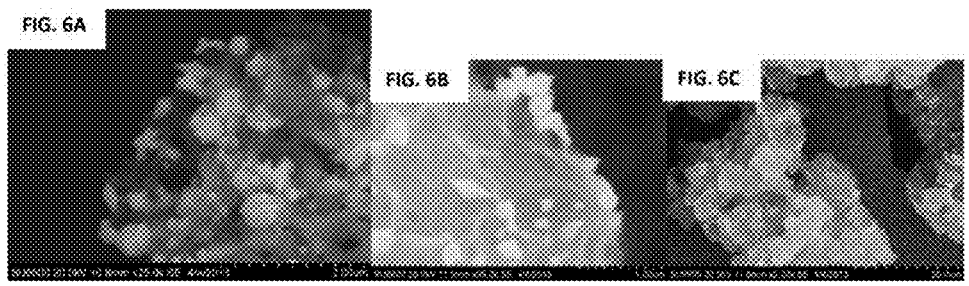
FIG. 6
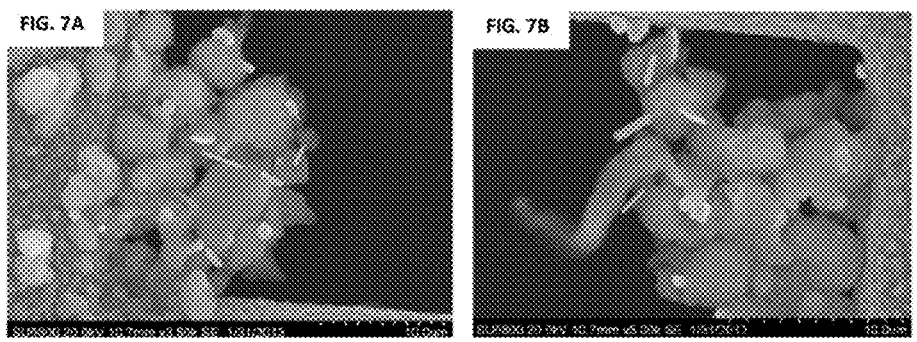
FIG. 7
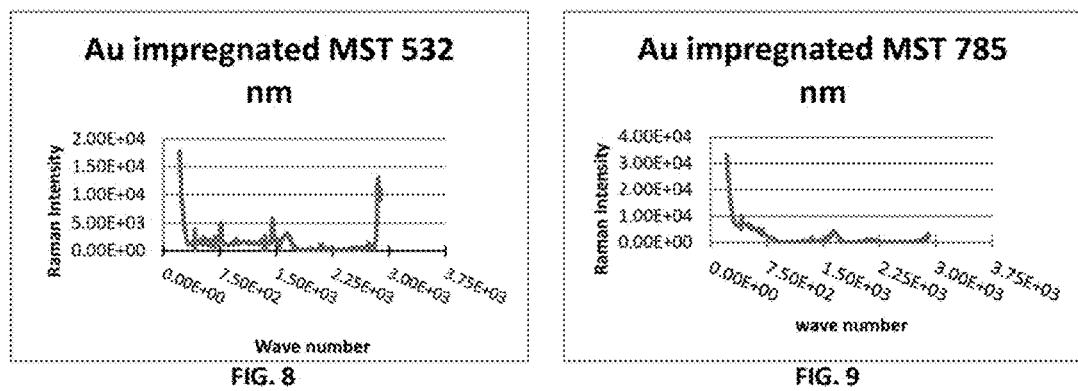

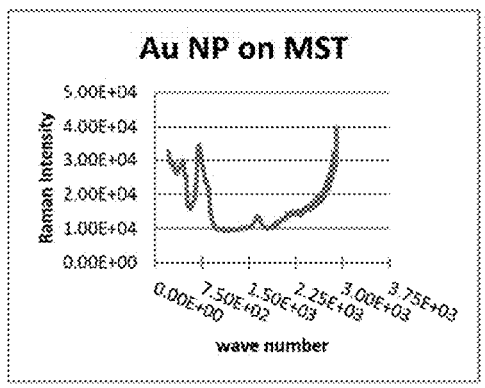
FIG. 10A
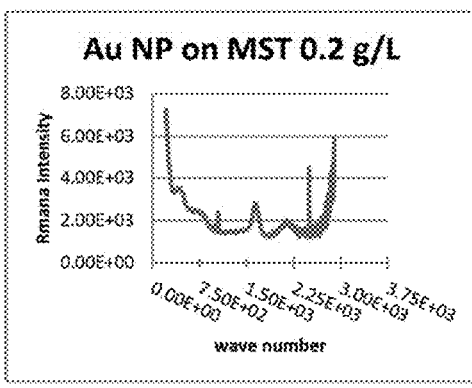
FIG. 10B
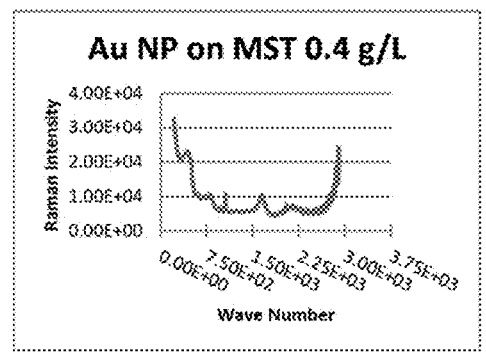
FIG. 10C
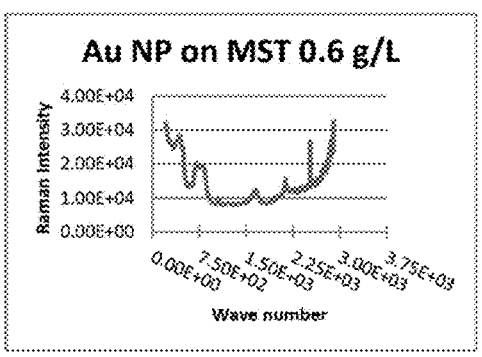
FIG. 10D
FIG. 10

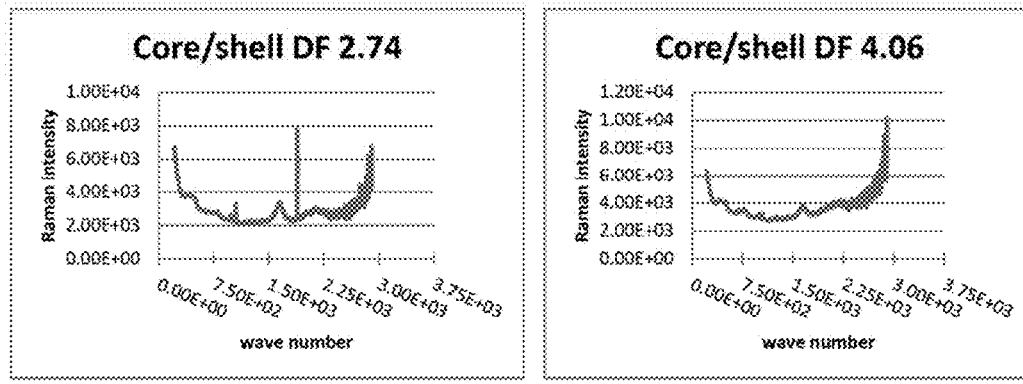
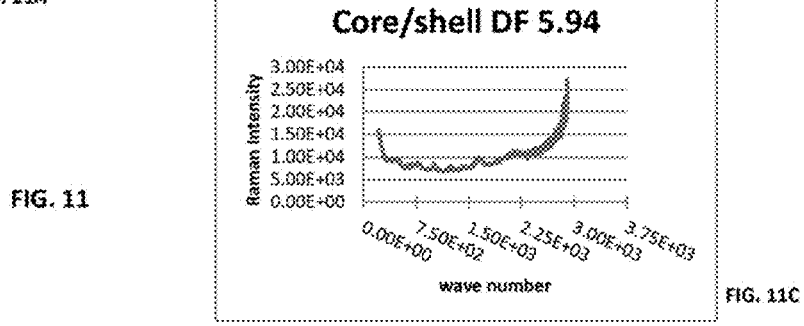
FIG. 11
FIG. 11A
FIG. 11B
FIG. 11C
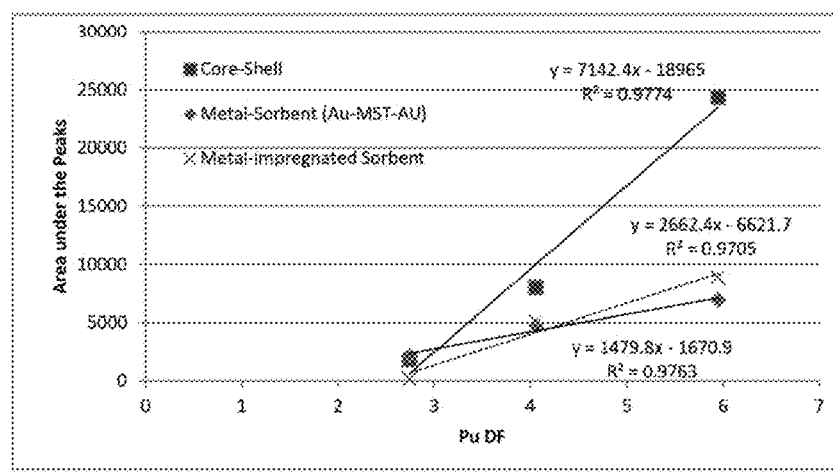
FIG. 12

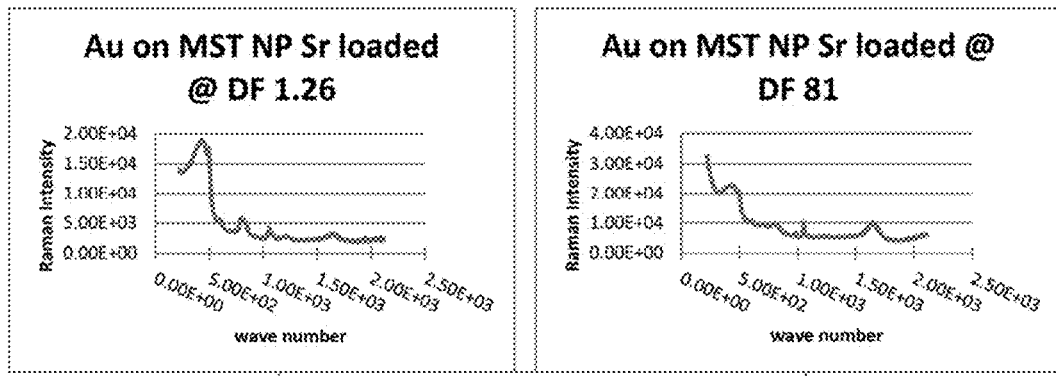
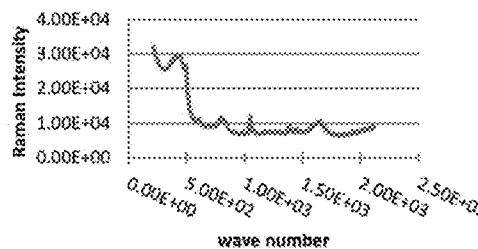
FIG. 13
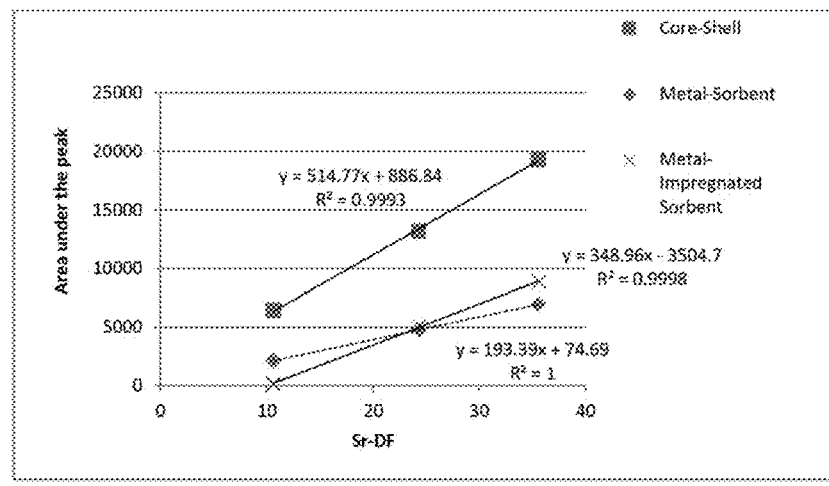
FIG. 14

METHODS AND MATERIALS FOR DETERMINATION OF DISTRIBUTION COEFFICIENTS FOR SEPARATION MATERIALS

FEDERAL RESEARCH STATEMENT

This invention was made with Government support under Contract No. DE-AC09-08SR22470 awarded by the United States Department of Energy. The Government has certain rights in the invention.

BACKGROUND OF THE INVENTION

In order to properly contain and process contaminant materials, it is necessary to understand not only what materials are being dealt with, but also the quantity of a contaminant in a particular location. As such, a variety of testing protocols and materials have been developed to identify and quantify compounds in waste facilities, storage facilities, ground water, etc. For instance, separation media including adsorbents, absorbents, and ion exchange media have been developed to identify and quantify contaminants that may be present in an area. To accurately identify and quantify any particular contaminant, however, it is necessary to know the affinity of that contaminant for a particular separation medium. Thus, the separation medium must itself be examined before it is possible to use with a high level of confidence.

In a typical method for determining the affinity of a species for a separation medium, an aliquot of a mixture that includes the species is separated and analyzed to determine the concentration of the species, and the remainder of the mixture is placed in contact with a separation medium, e.g., an ion exchange medium. Following a period of contact between the mixture and the separation medium, the solution and solid phases are separated by filtration, centrifugation, etc., and the solution is analyzed by an appropriate technique to determine the remaining concentration of the species. The difference between the initial concentration and that measured after some time interval is that assumed to have sorbed/exchanged onto the solid phase. Analysis of the solids, when pursued, requires additional handling prior to analysis. For instance, interstitial liquid must be removed by rinsing with an inert solution, the solids dried to constant weight and dissolved for analysis. The additional sample handling introduces additional experimental uncertainty and error. Furthermore, by taking aliquots from a test reaction composition, the phase ratio of liquid to solids may be inadvertently changed by an unknown amount if the sampling event does not remove a homogeneous aliquot. These methods are laborious and operationally complex, which can lead to error in accurate characterization of the media.

In view of the above, what is needed in the art is a simple, efficient, and reproducible method of determining the affinity of targeted species for separation media. For instance, a method for determining the distribution coefficient of a species for an ion exchange or sorbent medium that is faster and less expensive than current methods and that prevents errors as may come from excessive sampling and handling would be of great benefit.

SUMMARY

Aspects and advantages of the invention will be set forth in part in the following description, or may be obvious from the description, or may be learned through practice of the invention.

According to one embodiment, disclosed is a method for determining the distribution coefficient of a species for a separation material such as an ion exchange or sorbent material. A method can include separating a targeted species from a solution by use of a composite separation medium. The composite separation medium includes a separation material (e.g., an ion exchange material) and metal nanoparticles as a substrate for surface enhanced Raman spectroscopy (SERS). During the separation, the targeted species is distributed across a first phase and a second phase, the second phase including the composite separation medium. The concentration of the species in the first phase prior to the separation process can be known. Following the separation process, the second phase can be examined via SERS to determine the concentration of the species retained on/in the composite separation medium and thereby determine the distribution coefficient of the species for the separation material.

In one particular embodiment, the method can be utilized to determine the distribution coefficient of ionic hazardous waste materials such as actinides or strontium for an ion exchange medium to better characterize the medium for use in conjunction with the waste materials. The ability to carry out the method with a minimum of interaction with the waste materials can be particularly beneficial in such an embodiment.

Also disclosed is a method for forming a composite separation medium. For instance, a method can include suspending nano-sized seed particles in a solution that includes metal ions and a weak reducing agent and optionally also including a structure directing agent for a period of time such that metal nanoparticles develop over the time period as the seed particles are suspended in the solution. About 95% or more of the metal nanoparticles can have the same shape. As such, the metal nanoparticles can be ideally designed for use as an SERS substrate that can provide consistent, reliable data. The method also includes associating the metal nanoparticles with a separation material. For instance, the metal nanoparticles can be formed on a separation material or a coating of a separation material can be formed on the metal nanoparticles to form a composite separation medium for use in determining the distribution coefficient of a species for the separation material.

Also described are the composite separation media that can be formed and utilized as described here in. A composite separation media can include a separation material, e.g., a serpent or an ion exchange material, held in conjunction with metal nanoparticles as a substrate for SERS. The metal nanoparticles can have a high degree of similarity to one another, with about 95% or more of the nanoparticles having the same shape.

BRIEF DESCRIPTION OF THE DRAWINGS

A full and enabling disclosure of the present invention, including the best mode thereof, directed to one of ordinary skill in the art, is set forth in the specification, which makes reference to the appended figure, in which:

FIG. 1 is a scanning electron micrograph (SEM) image of gold nanorods formed according to disclosed methods.

FIG. 2 is a high resolution transmission electron microscope (HRTEM) image of the gold nanorods of FIG. 1.

FIG. 3 illustrates gold nanorods including a silica/titania shell with about 20 nm thickness.

FIG. 4 illustrates gold nanorods including a silica/titania shell with about 12 nm thickness.

FIG. 5 illustrates UV/Vis spectra of gold nanorods (10), gold nanorods including a 10 nm silica/titania shell (12), and gold nanorods including a 25 nm silica/titania shell (14).

FIG. 6 includes images (FIG. 6A, FIG. 6B, FIG. 6C) of gold nanoparticles formed on an ion exchange material.

FIG. 7 includes a first image (FIG. 7A) and a second image (FIG. 7B) showing hexagonal gold nanoparticles formed on an ion exchange material.

FIG. 8 presents the SERS data obtained at 532 nm excitation wavelength of a composite media including an ion exchange material and gold nanoparticles impregnated therein.

FIG. 9 presents the SERS data obtained at 785 excitation wavelength for the composite media of FIG. 8.

FIG. 10 presents the SERS data for a composite media including gold nanoparticles formed on a monosodium titanate (MST) ion exchange material (FIG. 10A), the same material following an ion exchange process with a simulated high level nuclear waste solution with the composite material at a concentration of 0.2 g/L (FIG. 10B), the same material following an ion exchange process with a simulated high level nuclear waste solution with the composite material at a concentration of 0.4 g/L (FIG. 10C), and the same material following an ion exchange process with a simulated high level nuclear waste solution with the composite material at a concentration of 0.6 g/L FIG. 10D.

FIG. 11 presents the SERS data for a composite medium having a core-shell structure include a gold core, an $SiO_2$ shell and an outer $TiO_2$ shell following ion exchange with a simulated high level nuclear waste having a measured plutonium decontamination factor (DF) of 2.74 (FIG. 11A), a DF of 4.06 (FIG. 11B) and a DF of 5.94 (FIG. 11C).

FIG. 12 graphically illustrates the linear relationship between the area under the SERS peaks and the plutonium decontamination factor for several different composite separation materials.

FIG. 13 presents the SERS data for a composite medium including gold nanoparticles formed on an MST particulate ion exchange material following an ion exchange process including strontium ion at a DF of 1.26 (FIG. 13A), a DF of 81 (FIG. 13B) and a DF of 90 (FIG. 13C).

FIG. 14 graphically illustrates the linear relationship between the area under the SERS peaks and the strontium decontamination factor for several different composite separation materials.

DETAILED DESCRIPTION OF THE INVENTION

It is to be understood by one of ordinary skill in the art that the present discussion is a description of exemplary embodiments only, and is not intended as limiting the broader aspects of the present disclosure. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

In general, disclosed herein are methods and materials for determining the affinity of separation materials for targeted species. More specifically, disclosed methods and materials can be utilized to determine the distribution coefficient of a species for the separation material after running a single separation protocol followed by examination of the separation material of the protocol according to SERS. Disclosed methods can be utilized to determine the affinity of existing separation materials for targeted species as well as to determine the affinity of newly engineered separation materials to characterize species.

The method utilizes composite separation media that combines a separation material of interest with a substrate for SERS that is in the form of metal nanoparticles. The metal nanoparticles used as the SERS substrate are highly uniform, and as such can generate highly consistent and dependable SERS data. By development and use of the highly uniform SERS substrate materials in the composite separation media, it has been found that the Raman signal obtained from the composite materials can be linearly correlated with the amount of the targeted species on/in the separation material. This approach provides a route to determination of distribution coefficients ($K_d$) for species that have affinity for the separation materials.

The metal nanoparticles utilized as the SERS substrate component of the composite separation materials can be formed of any metal capable of enhancing Raman scattering (e.g., silver, gold, aluminum, copper, etc.). It should be understood that while the present discussion is primarily directed to the formation and utilization of gold nanoparticles as SERS substrate in the composite separation media, the disclosure is not limited to gold nanoparticles, and any metal nanoparticles capable of enhancing the Raman scattering in an SERS protocol can be utilized as described.

Gold and silver nanoparticles are excellent substrates to detect materials with SERS techniques. In the present invention, light absorption for the Raman scattering can be tuned by use of nanoparticles with a well-defined shape such as, and without limitation, nano-stars, nano-rods, nanotubes, and nano-spherical designs.

In one embodiment, the nanoparticles can have an aspect ratio greater than one, as anisotropic metallic nanoparticles have characteristics that make them excellent candidates as SERS substrates. Plasmon absorption bands can be tuned by variation in the aspect ratio of the particles to be in resonance with common visible laser sources, optimizing the electromagnetic enhancement mechanism. Moreover, anisotropic nanoparticles can include highly curved, sharp surface features with dimensions less than 100 nm. This can increase the local electric field up to 100-fold at a tip, referred to as the "lightning rod effect". While the Raman affect itself is weak, the presence of the nanoscale metals in the composite separation media that efficiently interact with the incoming visible or NIR photon gives an enormous increase in the Raman signals of nearby molecules.

The metal nanoparticles used as a SERS substrate component of the composite separation media have a high degree of conformity. For instance about 95% or more, about 97% or more, or about 99% or more, of the metal nanoparticles can have the same shape. In addition, the metal nanoparticles can be highly similar with regard to size. By way of example, the metal nanoparticles can have a cross-sectional dimension standard deviation of about ±2 nanometers (nm) or less, or about ±1 nm or less in some embodiments. The high degree of conformity of the nanoparticle SERS substrate can provide the nanocomposite materials with tailored and tunable structural, optical and surface properties. For instance, the optical properties can be tuned extensively by the shape of the metal nanoparticles. For gold and silver nanoparticles, multiple plasmon bands that give rise to visible colors can occur in the visible and into the infrared for various geometries, including nanorods, nanostars and nanoshells. Furthermore, the ability to tune the plasmon band of nanorods by changing their aspect ratio to a specific laser excitation wavelength allows for maximum SERS enhancement.

The composite separation media can include the SERS substrate and the separation material in different configurations. One exemplary configuration includes surface decoration of the separation material with the metal nanoparticles. The geometry and the size of the components (the separation material and the SERS substrate particles) can be tailored to tune the properties of the composite separation media. For instance, the separation material can be presented in the form of nano-, micro-, or macro-sized particles with a well-defined surface area to volume ratio. Similarly, the size and shape of the metal nanoparticles can be tailored to provide well-defined optical properties and consistent SERS characteristics.

The relative amount of the SERS substrate that decorates an underlying separation material can be controlled to prevent interference with the interaction between the separation material and the targeted species. A composite separation media that includes an external SERS substrate can include the metal nanoparticles in an amount such that the SERS process is highly efficient without interfering with removal of the species by the separation material. For example, the composite separation media can include the metal nanoparticle SERS substrate in an amount of about 50% or less by weight of the composite material, for instance from about 10% by weight to about 40% by weight, in some embodiments.

According to another embodiment, the composite separation media can include the separation material external to the SERS substrate. In this embodiment, the media can describe a core/shell structure with the separation material forming a partial or total external shell over an underlying layer or core of the SERS substrate material. The underlying material of the composite media can include the SERS substrate material as a solid core, e.g., solid gold nanoparticles, or can include multiple layers. For instance, an inner core of the composite material can include a single layer of the SERS substrate, and an outer coating layer of the separation material can then be formed on the SERS substrate. Any number of layers is encompassed in a core/shell composite media, including structures having a hollow core, e.g., a gold nanoshell and an external coating of the separation material.

In the core/shell design, the thickness of the external layer of the separation material can be controlled, which can be used to tailor the characteristics of the separation material (e.g., the surface area to volume ratio of the material) as well as to tailor the optical properties of the underlying SERS substrate. Thus, this orientation can offer routes to tailor the composite media to possess unique and useful characteristics.

Independent of the physical orientation of the separation material and the SERS substrate, the composite separation media can include an SERS substrate in the form of metal nanoparticles having a high degree of similarity to one another and can include a separation material at a location at which it can interact with the targeted species in a separation protocol.

In forming the composite media, the SERS substrate nanoparticles can be formed by use of initially formed "seed" particles that may differ from the latter-formed SERS substrate particles by size, shape, and or material. The seed particles can be, for example, about 5 nm or less in cross sectional dimension, for instance from about 1 nm to about 4 nm in cross sectional dimension in some embodiments.

Depending upon the final morphology of the composite separation media, the seed particles can be formed as free particles unassociated with other materials in an aqueous suspension or alternatively can be formed on an underlying substrate. For instance, in those embodiments in which the composite separation media is in the form of a separation material externally decorated with the metal nanoparticles, the seed particles can be formed onto the surface of the separation material.

A wet chemical process can be utilized to form the seed particles. Basically, the process can include reduction of an aqueous solution of a metal salt with a strong reducing agent optionally in conjunction with a surfactant to yield spherical seed particles of the metal of the metal salt. Beneficially, the process can be carried out at standard temperature and pressure in an air atmosphere.

The metal salt can be any salt that exhibits water solubility at room temperature. For instance, a chloride salt of gold such as gold (III) chloride trihydrate ($H_6AuCl_3O_3$), gold(III) chloride ($Au_2Cl_6$), or chloroauric acid ($HAuCl_4$). Any gold salt including gold with an oxidation state of 3+ can be utilized including, without limitation, NaAuCl4, KAuCl4, etc. Variation in the gold salt can be utilized in one embodiment to vary and control the size, shape, etc. of the products. In formation of silver nanoparticles, a silver salt as is known in the art can be utilized to provide the silver ions such as, without limitation, a nitrate salt of silver (e.g., $AgNO_3$) or the like.

A solution can include the metal salt at a concentration of from about $10^{-2}$ M to about $10^{-6}$ M in some embodiments, for instance from about $10^{-3}$ M to about $10^{-5}$ M, or from about $10^{-3}$ M to about $10^{-4}$ M, such as about $1.25 \times 10^{-4}$ M in one embodiment.

A strong reducing agent can be combined with the metal ions in an aqueous solution to instigate reduction of the metal and formation of the nanoparticles. As utilized herein, the term "strong reducing agent" generally refers to a material having reduction potential of about −0.5V or less at a somewhat acidic pH (e.g., about 5) Examples of strong reducing agents can include, without limitation, inorganic compounds, i.e., hydrides of the alkaline earth metals, such as $BeH_2$, $MgH_2$, $CaH_2$, $SrH_2$, and $BaH_2$; alkali metal aluminum hydrides such as $LiAlH_4$, $NaAlH_4$, $KAlH_4$, $RbAlH_4$, and $CsAlH_4$; borohydrides of the alkali metals and other metals, such as $LiBH_4$, $NaBH_4$, $KBH_4$, $RbBH_4$, $CsBH_4$, $Mg(BH_4)_2$, $Be(BH_4)_2$, and $Al(BH_4)_3$ and alkali metal hydrides such as NaH, KH and LiH. The strong reducing agents that may be used also include organometallic compounds such as trialkyl aluminum compounds, alkyl aluminum hydride compounds, aluminum alkoxide compounds and other organometallic compounds. The trialkyl aluminum compounds and the alkyl aluminum hydride compounds have some structural similarities. In these compounds the alkyl group is a hydrocarbyl group that can contain from 1 to about 14 carbon atoms. Illustrative of such compounds are trimethylaluminum, triethylaluminum, diethylaluminum, triisobutyl aluminum, tridecylaluminum, and tridodecylaluminum. Combinations of reducing agents are also encompassed herein.

The concentration of the strong reducing agent can be utilized to define and control the characteristic of the nanoparticles. For instance, by varying the concentration of the strong reducing agent at a concentration by a factor of 10, for instance from about 6 mM to about 60 mM to about 600 mM, the size of the product nanoparticles can be varied.

According to one embodiment, a solution can be formed including the metal ions combined with the strong reducing agent, and over a period of time (for instance about 30 minutes or more, for example from about 30 minutes to about 1 day), the metal can be reduced and the seed nanoparticles can form as a suspension in the solution.

In those embodiments in which the composite separation medium includes the separation material externally decorated with the metal nanoparticles, the metal nanoparticles can be formed on the separation material. For instance, a suspension of a separation material in the form of nano- or micro-sized particles, examples of which are described herein, can be combined with the metal salt and the reducing agent and over a period of time the metal ions can be reduced and the seed nanoparticles can form on the particles of the separation material.

Optionally, a formation solution can include a cationic surfactant, for instance at a concentration of about 0.1 M. Examples of cationic surfactants can include, without limitation, a quaternary ammonium surfactant such as cetyltrimethylammonium bromide (CTAB) a.k.a. hexadecyl trimethyl ammonium bromide, and other alkyltrimethylammonium salts such as cetyltrimethylammonium chloride (CTAC), Cetylpyridinium chloride (CPC), polyethoxylated tallow amine (POEA), benzalkonium chloride (BAC), benzethonium chloride (BZT), etc.

Following formation of the seed nanoparticles, the metal nanoparticles of the SERS substrate can be formed through combination of a growth solution containing additional metal salt and a weak reducing agent with the seed nanoparticles. Optionally, the solution can also include a structure-directing agent and/or a cationic surfactant. Variations in reaction conditions such as ratio of the seed particles to the metal ion concentration, presence and concentration of a structure-directing agent, etc. can be used to control the final morphology and size of the metallic nanoparticles. In general, the metal nanoparticles can be larger than the seed particles. For instance, the metal nanoparticles can have a maximum cross sectional dimension of about 200 nm or less, for instance from about 10 nm to about 200 nm, or from about 100 nm to about 150 nm in some embodiments. Moreover, through variation in the reaction characteristics anisotropic metallic structures, e.g. stars, rods, etc. can be formed.

The metal ions can be provided by use of the same or different metal salts as utilized in forming the seed particles. In general, the metal salts can be provided to the formation solution in a concentration of from about $10^{-2}$M to about $10^{-6}$M. In addition, the metal ions can generally be provided to the formation solution in a ratio to the seed particles of from about 1:10 to about 1:100. As previously discussed, such characteristics of the formation solution can be varied to vary the size and/or morphology of the metal nanoparticles.

Weak reducing agents can generally include reducing agents having a reduction greater than that of the strong reducing agents as defined above, e.g., about −0.5V or greater at slightly acidic conditions. Examples of weak reducing agents may include, without limitation, ascorbic acid, diols, citric acid, fructose, amine compounds, α-hydroxy ketone compounds, succinic acid, maltose, etc. The weak reducing agents can be used in single or in combination, and are generally present in the formation solution in an amount of from about $10^{-2}$ mM to about 10 mM, for instance from about 0.1 mM to about 1 mM or about 0.5 mM in some embodiments.

Addition of a structure-directing agent in conjunction with a bromine containing cationic surfactant (e.g., CTAB) can in one embodiment encourage the formation of anisotropic nanoparticles as well as control of the nanoparticle size. A structure directing agent can generally include a metal ion such as, and without limitation, silver ions, copper ions, iron ions, etc. In one embodiment, the structure-directing agent can be silver ions. For example, the formation solution can include silver ions (e.g., obtained by addition of a metal salt to the solution) in an amount of from about $2 \times 10^{-5}$ M to $10 \times 10^{-5}$ M.

Metal nanoparticles having a tailored morphology and size can be formed for use as an SERS substrate by the seed-mediated wet chemistry method. FIG. 1 illustrates gold nanorods as may be formed by the method. FIG. 2 is another image of the gold nanorods obtained via HRTEM. As can be seen, the gold nanoparticles are highly uniform in both shape and size. For instance, in this particular embodiment, the gold nanorods have a length of 48±2 nm and a width of 19±1 nm.

Through modification of the formation parameters, various morphologies can be developed for the metal nanoparticles. For example, FIG. 6 and FIG. 7 present images of gold nanoparticles in a variety of morphologies and sizes as may be formed.

In conjunction with the metal nanoparticles, the composite separation media can include a separation material. The separation material can generally be any sorbent or ion exchange material capable of adherence to the metal nanoparticles. In one embodiment, the separation material can include an ion exchange material, and in one particular embodiment, an ion exchange material as may be utilized in examining hazardous materials that can be present in a solution, e.g., actinides or strontium. However, the separation material is not limited to such, and other separation materials are encompassed herein. Exchange materials can be organic or inorganic and can interact with a targeted species via adsorbency, absorbency, ion exchange, charge/charge interaction, covalent or non-covalent bonding, or any other interaction chemistry including combinations of interaction chemistries.

Inorganic ion exchange materials can include titanates and hydrous titanium oxides. In one embodiment, crystalline sodium titanates belong to the series $Na_4Ti_nO_{2(n-2)}$ (e.g., with n=1, 3, 5, 9) can be utilized. Hexacyano ferrate-based ion exchange materials are encompassed, which have been developed for the selective separation of cesium from a wide variety of nuclear waste solutions, and may be examined according to the present disclosure for a variety of separation applications.

In one embodiment, the composite separation media can include monosodium titanate as the separation material. Monosodium titanate is a white, inorganic, and amorphous sodium titanate that can have the general composition of $HNaTi_2O_5 \cdot xH_2O$ where x is about 2 to about 4. The materials can exhibit high selectivity for sorbing various metallic ions over a wide pH range extending from about pH 2 to more than pH 14.

A titanate separation material can be a peroxo-titanate, which can be formed by treatment of monosodium titanate with a peroxide to convert the monosodium titanate to a peroxo-titanate form, which has been shown to improve the sorption capabilities of materials. The general formula of a peroxo-titanate as may be utilized as a separation material is $H_vNa_wTi_2O_5 \cdot (xH_2O)[yH_zO_2]$ where v+w=2 and z=0 to 2. For peroxo-titanates synthesized under neutral or basic conditions, v≈w≈1. For acid-treated peroxo-titanates, v>w.

The peroxide species is most likely coordinated to the titanium and may be present as $O_2^{2-}$, $HO_2^-$, or $H_2O_2$ (see Nyman, et al., Chem. Mater. 2006, 18, 6425-6435). In one embodiment, peroxide treatment of a monosodium titanate material can be carried out according to methods as described in U.S. Pat. No. 7,494,640 to Nyman, et al., which is incorporated herein by reference.

Ion exchange materials such as hydrous titanium oxides and titanates can be formed according to any suitable process, with a preferred process generally depending upon the desired form of the composite separation media, i.e., whether the ion exchange material is to be utilized as a supporting substrate for the metal nanoparticles or alternatively, whether the ion exchange material is to be supported on the metal nanoparticles, with the metal nanoparticles as a component of the core of the core/shell morphology.

Exemplary methods for forming titanium-based ion exchange materials can include, but are not limited to the following:

1) Precipitation of hydrous titanium oxides from aqueous titanium solutions, especially $TiCl_4$, with alkali solutions, especially NaOH, at room temperature. Sol-gel methods can be used, in which better mixing of the reagents can be obtained by mixing titanium alkoxide with NaOH dissolved in alcohol. This process results in the formation of a soluble titanate intermediate, which can be precipitated by adding water.

2) Boiling of amorphous products from the precipitation of $TiCl_4$ with NaOH or other solid hydrous titanium oxides, such as hydrous anatase, in concentrated NaOH solution.

3) Hydrothermal treatment of amorphous products from the precipitation of $TiCl_4$ with NaOH or other solid hydrous titanium oxides, such as hydrous anatase or a sol-gel product, in concentrated NaOH solution. Rather high temperatures, 200-500° C., and pressures, 20-400 bars, are needed for the hydrothermal treatment.

4) Solid state synthesis of crystalline titanates, such as $Na_2Ti_6O_7$, from solid titanium compounds, such as $TiO_2$, and a sodium salt, such as $Na_2CO_3$, at high temperatures, e.g., 700-1100° C.

Organic anion exchange materials can be combined with an SERS substrate as described. For instance, water-insoluble macroporous beads comprising organic polymers having ionizable base groups (e.g., amines) attached to the polymer chains can be utilized. In one embodiment, the polymers can be crosslinked copolymers of styrene, such as crosslinked copolymers of styrene/divinylbenzene with the base groups attached to the aromatic rings of the polymer chain. Such anion exchange resins are commercially available, e.g., from The Dow Chemical Company under the tradename DOWEX® and from Rohm and Haas Company under the trade name AMBERLYST®. Reillex® HPQ Polymer is a crosslinked poly-4-vinylpyridine macroporous polymer available from Vertellus that is a strong base polymer (quaternary version of Reillex® HP Polymer) finding use in the removal and purification of anionic materials such as radioactive materials in nuclear fuels. Other examples of organic anionic exchange materials as may be utilized as describe herein include resorcinol-formaldehyde resins.

Organic cation exchange resins as may be combined with an SERS substrate can be similar in structure to anion exchange resins described above, except that instead of base groups the cation exchange resins can include ionizable pendent acid groups. Such resins are commercially available from, e.g., the sources given above. Example of cation exchange resins include Duolite® GT-73 and Amberlite® IRC-718 available from Supelco (Bellefonte, Pa.), and BIO-FIX® available from Rahco Environmental Services (Spokane, Wash.).

Anion and cation exchange resins may be obtained in their neutral salt forms, the base groups may be, e.g., in their $Cl^-$ or $OH^-$ forms and the acid groups may be, e.g., in their $H^+$ or $Na^+$ forms as is known in the art.

In one embodiment, an organic ion exchange resin can include an inorganic compound in combination with the organic resin. For instance, a combination organic/inorganic ion exchange material can be prepared by incorporating one or more soluble compounds of titanium and/or zirconium, then adding an alkalizing agent to cause precipitation of such titanium and/or zirconium as oxide hydrates. Initially, solubility of the titanium and/or zirconium compounds may be improved, if needed, by having the aqueous solution in the acid range, e.g., aqueous HCl. The titania hydrate or zirconia hydrate can optionally be converted to hydrated titanium phosphate or hydrated zirconium phosphate by reaction with soluble phosphate compounds.

Another classification of separation materials as may be examined according to the disclosed methods are sorbent clays including both absorbent and adsorbent clays. Absorbent clays are distinct from adsorbent clays in that clays that adsorb water only take up water onto their surface, while absorbent clays can take water into the structure of the clay itself.

Examples of adsorbent clays include those in the mica-illite group, three-layer-minerals such as pyrophylite, muskovite, dioktaedric illite, glaukonite, talc, biotite, and dioktaedric illite.

Examples of absorbent clays include two-layer-minerals of the kaolinite-group such as kaolinite, dickite, halloysite, nakrite, serpentine, greenalithe, berthrierine, cronstedtite, and amesite. Smectite-group three-layer minerals can also fall within the scope of an absorbent clay. Smectite-group three-layer minerals include dioktaedric vermiculite, dioktaedric smectite, montmorillonite, beidellite, nontronite, volkonskoite, trioctaedric vermiculite, trioctaedric smectite, saponite, hectorite, and saukonite. Salt forms of minerals can also be included within the scope of absorbent clays. Absorbent clay salts generally have potassium, calcium or magnesium counterions but can also have organic counterions.

In one embodiment, the separation material can be in the form of micron-sized or nano-sized particulate. A nano-sized particulate can exhibit spherical-shaped particle morphology with a monodisperse distribution of particle diameters. For instance, the maximum particle cross-sectional dimension can be about 1000 nm or less, about 500 nm or less, or about 300 nm or less in some embodiments. For example, the maximum particle cross sectional dimension can be in the range from 100 to 150 nm. A micron-sized separation material can optionally be utilized. A micron-sized titanate carrier can generally have a maximum cross-sectional area of from about 1000 nanometer to about 1 millimeter. Of course, the separation material is not limited to particulate separation materials, and other forms including, without limitation, fibers, films, gels, etc. are encompassed herein.

In those embodiments in which the composite separation media includes the separation material as a substrate base upon which the metal nanoparticles are applied, the formation method can generally include forming the nanoparticles in an environment that includes the separation material such that the nanoparticles precipitate from solution onto the separation material. For instance, a suspension of particulate ion exchange or sorbent can be formed or provided, and a metal nanoparticle formation process as previously described can be carried out in the presence of the particulate separation material to form the highly uniform SERS substrate on the surface of the separation material.

In those embodiments in which the SERS substrate serves as a carrier for the separation material in a core/shell morphology, the nanoparticles can be first formed followed by formation of separation material on the nanoparticles. For instance, a precipitation or polymerization process can be carried out in the presence of the metal nanoparticles such that the separation material is deposited on the surface of the nanoparticles. Through control of the process parameters, the shell thickness can be tightly controlled. In general, a shell of a core/shell separation material should be of a thickness that does not interfere with the SERS performance of the nanoparticles. For instance, a separation material shell can generally be about 50 nm or less in thickness, for example from about 5 nm to about 40 nm or from about 3 nm to about 20 nm in some embodiments. The resulting core/shell nanomaterials can be stable and can be isolated without core aggregation or decomposition.

The thickness of the shell can be controlled by adjusting the growth conditions, including reactant concentrations. By way of example, FIG. 3 illustrates core/shell nanoparticles including a gold core and a silica/titania shell of about 20 nm and FIG. 4 illustrates core/shell nanoparticles including a gold core of the same size and a silica/titania shell of about 12 nm. In these embodiments, the shell thickness was controlled through modification of the reactant concentrations in the growth media.

Through control of the size of the metal nanoparticles as well as the presence and thickness of a shell formed on the metal nanoparticles, the optical properties of the SERS substrate can be finely tuned. For instance, FIG. 5 presents the UV-Vis spectra of the gold nanorods of FIG. 1 and FIG. 2 at 10 as well as that of the core/shell particles of FIG. 3 at 12 and that of the core/shell particles of FIG. 4 at 14. As can be seen, the gold nanorods exhibit two plasmon bands: longitudinal and transverse. This is due to the nanorods ability to absorb and scatter light along multiple axes: the long axis (longitudinal plasmon band) and the short axis (transverse plasmon band) at around 660 nm and 520 nm, respectively. Both the longitudinal plasmon band at ~660 nm and transverse plasmon bands at ~520 nm appear to red-shift with increasing silica/titania shell thickness deposition, consistent with theoretical predictions in the literature, which correlate this observation with an increase in the local dielectric constant surrounding the gold nanorods that is due to silica/titania shell.

The composite separation media may be tuned for a specific excitation wavelength. For instance, FIG. 8 and FIG. 9 present the SERS data for a composite separation medium that includes gold impregnated monosodium titanate nanoparticles at two different excitation wavelengths, 532 nm and 785 nm, respectively. As illustrated the SERS results vary between the two different excitations. Tuning of the composite separation material to demonstrate a higher SERS response within a particular wave number range can enhance the response when examining the composite material following loading of the targeted species.

Following formation, the composite separation media may be utilized to determine a distribution coefficient of a particular species for the separation material. A separation protocol can be carried out according to typical practice with the separation material, with no variation in the protocol necessary due to the presence of the SERS substrate held in conjunction with the separation material. For instance, a starting solution including the targeted species at a known concentration can be formed. The solution can then be subjected to a typical separation protocol using the composite separation media, e.g., an ion exchange process utilizing a separation column as is known in the art. Following the separation protocol, the sorbent phase of the separation that includes the composite separation media can be removed from the column and examined according to a SERS process. The resulting data can provide information with regard to the concentration of the species on the composite separation media. Through utilization of the highly uniform metal nanoparticles as the SERS substrate, it has been found that there can be a linear relationship between the area under the SERS peaks and the analyte concentration. Thus, the data can be utilized to determine the distribution coefficient of the species for the particular separation media employed.

The present application may be further understood by reference to the following Examples.

EXAMPLE 1

Gold nanorods were grown on pre-formed gold nano-seeds in the presence of surfactant, CTAB, and a small amount of silver ions. Initially, 1.5 nm-diameter gold nano-seed nanoparticles were formed by reduction of $AU^{3+}$ ions in the presence of a strong reducing agent, sodium borohydride. In a typical experiment, a $2.5\times10^{-4}$ M solution of $HAuCl_4$ was prepared in 0.1M CTAB. $NaBH_4$ (600 mL, 10 mM) was added to the gold/CTAB solution (10 mL) with vigorous stirring for 10 min to precipitate the gold nano-seeds.

The gold nano-seeds were then used as templates to form the larger anisotropic nanoparticles. The following aqueous solution was prepared: CTAB solution (9.5 mL, 0.1 M), silver nitrate solution (50 □L, 10 mM), and chloroauric acid (0.5 mL, 10 mM). To this solution ascorbic acid (0.55 □L, 0.1 M) was added with gentle mixing. Finally the seed solution (12 □L) was added and the entire solution was mixed and then left undisturbed overnight (14-16 hours). Silver ions were used to control the shape, size and aspect ratio of the resulting Au nanorods.

SEM analysis of the gold nanorods demonstrated that the silver assisted seed mediated approach produced nanomaterials with very good size and shape uniformity (FIG. 1). The gold nanoparticles were found to have a length L of 48±2 nm and a width d of 19±1 nm with ~95% of the nanorods having the same size and shape. High resolution TEM (HRTEM) was used to characterize the lattice arrangement and crystallinity of the Au nanorods. HRTEM images of the nanorods display well-defined, continuous and equally-spaced fringe patterns for their atomic lattice (FIG. 2).

After preparation and purification, the anisotropic gold nanorods were coated with a silica-titania shell through an indirect coating method. 25□ □L of a 0.5 mM solution of mercaptopropyl trimethoxysilane ($HS(CH_2)_3Si(OCH_3)_3$, MPTMS) was added to a 1 mL aliquot of the gold nanoparticles. The resulting solution was then stirred for 1 hr to ensure that MPTMS was bound to the gold nanoparticles. Following, 10□ □L, of a 0.252 M stock solution of sodium silicate ($Na_2O(SiO_2)_3$) followed by a 0.5 mM solution of titanium isopropoxide (5-50 □L, in different sample runs) was added and the stirring was continued for another 20 min. The final solution was allowed to sit for 24 hrs.

The silica dielectric network between the metallic nanoparticle and $TiO_2$ semiconductor increased physical separation and electrical isolation and reduced premature recombination of the electron-hole charges.

Microscopy studies (FIG. 3, FIG. 4) show that silica/titania shell was uniform along the entire length of the gold nanorods and that the rods were completely encapsulated within silica/titania shell. Discrete, non-agglomerated nanocomposite particles with homogeneous shells were produced.

EXAMPLE 2

Spherical micro- and nano-titanates and nanotubes were prepared by sol-gel approaches described elsewhere. Light absorption for these materials was tuned by surface decorations of gold or silver nanoparticles of either nano-star, nano-rod, or nano-spherical designs.

Surface modification of the titanates structures were achieved by a seed mediated approach. A $2.5\times10^{-4}$ M $HAuCl_4$ solution in which the salt was dissolved in the presence of 0.1 M CTAB was reduced by $NaBH_4$ (600 mL, 10 mM) at ambient temperature in air to yield 3.5-4 nm spherical seed particles precipitated onto the MST substrates.

Next, a growth solution was formed containing chloroauric acid (0.225 mL, 10 mM), a structure-directing silver nitrate (129 □L, 5 mM), and CTAB (9.5 mL, 0.1 M). To this a solution of ascorbic acid (0.55 □L, 0.1 M) as weak reducing agent, was added with gentle mixing. Finally seed solution (12 □L of the gold nanoparticle decorated MST) was added and the entire solution was mixed and then left undisturbed overnight (14-16 hours).

The structural information such as the size, shape, thickness (length), aspect ratio, porosity, separation, and topology of different composite structures were examined by multiple characterization techniques including transmission electron microscopy (TEM), field emission scanning electron microscopy (SEM) and light scattering UV/Vis spectroscopy. The final composition and metal surface distribution on nanomaterial's surface was determined using energy dispersive X-ray analysis (EDX) and EDX mapping. X-Ray energy dispersive microanalysis of hybrid colloids was performed to reveal their composition. These results (data not shown) confirmed clearly that the wet chemical reaction occurred and the resulting products were Au-silica-titania hybrid nanostructures.

EXAMPLE 3

A variety of composite separation media each with a different morphology was evaluated for ability to be effective substrates for sorption and SERS experiments.

FIG. 10A illustrates the SERS data for gold-MST composite separation media prior to any sorption experiments. FIG. 10B, FIG. 10C, and FIG. 10D present the SERS results following ion exchange protocols with high level nuclear waste simulant solutions including the composite separation media at concentrations of 0.2 g/L (FIG. 10B), 0.4 g/L (FIG. 10C), and 0.6 g/L (FIG. 10D).

Additional separation protocols were run for core-shell samples including a gold core, a first $SiO_2$ layer and an outer $TiO_2$ layer. FIG. 11 provides 3 plots showing the SERS results for these materials following ion exchange protocols with high level nuclear waste simulant solutions including the composite separation media at concentrations of 0.2, 0.4, and 0.6 g/L, which resulted in Pu decontamination factors of 2.74 (FIG. 11A), 4.06 (FIG. 11B), and 5.95 (FIG. 11C).

FIG. 12 graphically illustrates the area under the peaks for the SERS data for separation of plutonium solutions with these different decontamination factors for three different morphologies of composite separation media. As can be seen the SERS data is linear with a high $R^2$ value for each morphology.

FIG. 13A illustrates the SERS data for a solution at a Sr decontamination factor of 1.26, FIG. 13B illustrates the SERS data for a solution at a Sr decontamination factor of 81, and FIG. 13C illustrates the SERS data for a solution at a Sr decontamination factor of 90.

FIG. 14 graphically illustrates the area under the peaks for the SERS data for separation of strontium solutions with different decontamination factors for three different morphologies of composite separation media. As can be seen the SERS data is linear with a high $R^2$ value for each morphology.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method for determining the distribution coefficient of a targeted species for a separation material comprising:
    contacting a solution comprising the targeted species at a known concentration with a composite separation medium, the composite separation medium including first particles comprising a separation material at a surface of each of the first particles and the composite separation medium further including a surface enhanced Raman spectroscopy (SERS) substrate, the SERS substrate including metal nanoparticles in which 95% or more of the metal nanoparticles have an identical shape and in which the metal nanoparticles have a cross-sectional dimension standard deviation of ±2 nanometers (nm) or less, wherein upon the contact, a portion of the targeted species becomes retained on the composite separation medium;
    following the contact, examining the composite separation medium according to an SERS process;
    determining by the examination a total concentration of the targeted species retained on the composite separation medium; and
    determining from the known concentration and the retained concentration the distribution coefficient of the targeted species for the separation material.

2. The method of claim 1, wherein the separation material is an ion exchange material.

3. The method of claim 2, wherein the separation material is an anion exchange material.

4. The method of claim 1, wherein the targeted species comprises actinides or strontium.

5. The method of claim 1, wherein the metal nanoparticles comprise gold nanoparticles.

6. The method of claim 1, wherein the composite separation medium includes a plurality of the metal nanoparticles at the surface of each of the first particles.

7. The method of claim 1, wherein the first particles comprise core/shell particles, the core/shell particles including the separation material as an outer layer of the core/shell particles, the core of each of the core/shell particles including one of the metal nanoparticles.

8. The method of claim 1, wherein the solution comprising the targeted species is a waste solution or a ground water solution.

9. The method of claim 1, the composite separation medium comprising the metal nanoparticles in an amount of about 50% or less by weight of the composite separation medium.

10. The method of claim 1, wherein the first particles comprise microparticles.

11. The method of claim 1, the separation material comprising a titanate or a hydrous titanium oxide.

12. The method of claim 11, the separation material comprising a sodium titanate.

13. The method of claim 11, the separation material comprising monosodium titanate or a peroxo-titanate.

14. The method of claim 1, wherein the SERS process comprises the analysis of an area under an SERS peak, wherein the total concentration of the targeted species and the area under the SERS peak describes a linear relationship for quantitative analysis.

15. The method of claim 1, wherein the metal nanoparticles comprise silver nanoparticles.

16. The method of claim 1, wherein the metal nanoparticles comprise copper nanoparticles.

* * * * *